United States Patent
Kimbahune et al.

(10) Patent No.: US 10,813,571 B2
(45) Date of Patent: Oct. 27, 2020

(54) DEVICES AND METHODS FOR NON-INVASIVE MONITORING OF SUBSTANCE IN A BODY

(71) Applicant: TATA CONSULTANCY SERVICES LIMITED, Mumbai (IN)

(72) Inventors: Sanjay Madhukar Kimbahune, Maharashtra (IN); Sunil Kumar Kopparapu, Maharashtra (IN); Syed Mohammad Ghouse, Maharashtra (IN); Pankaj Harish Doke, Maharashtra (IN)

(73) Assignee: Tata Consultancy Services Limited, Mumbai (IN)

( * ) Notice: Subject to any disclaimer, the term of this patent is extended or adjusted under 35 U.S.C. 154(b) by 278 days.

(21) Appl. No.: 16/004,177

(22) PCT Filed: Dec. 12, 2016

(86) PCT No.: PCT/IB2016/057537
§ 371 (c)(1),
(2) Date: Jun. 8, 2018

(87) PCT Pub. No.: WO2017/098485
PCT Pub. Date: Jun. 15, 2017

(65) Prior Publication Data
US 2018/0360345 A1    Dec. 20, 2018

(30) Foreign Application Priority Data
Dec. 10, 2015 (IN) .......................... 4655/MUM/2015

(51) Int. Cl.
*A61B 5/08* (2006.01)
*A61B 5/093* (2006.01)
(Continued)

(52) U.S. Cl.
CPC ............ *A61B 5/082* (2013.01); *A61B 5/0803* (2013.01); *A61B 5/0935* (2013.01);
(Continued)

(58) Field of Classification Search
CPC ......... A61B 5/08; A61B 5/0803; A61B 5/097; A61B 5/72; A61B 5/7271; G01N 33/497; G01N 33/4975
See application file for complete search history.

(56) References Cited

U.S. PATENT DOCUMENTS

2006/0122864 A1\* 6/2006 Gottesman ............. G06Q 50/22
                                                  600/300
2007/0258894 A1   11/2007 Melker et al.
(Continued)

Primary Examiner — Eric F Winakur
(74) Attorney, Agent, or Firm — Finnegan, Henderson, Farabow, Garrett & Dunner, LLP (57) ABSTRACT

Devices and methods are provided for non-invasive goal oriented and personalized monitoring of substance consumption directed towards aiding reduction of substance intake by a user. Based on the substance consumption characteristics and the user's profile, the user's substance consumption profile is identified and average amount of the substance in the body at a given time is computed. A threshold corresponding to amount of substance the body can sustain is then computed based on goals set by the user and the substance consumption characteristics and the user's profile. Alerts can be generated and transmitted to the user based on pre-determined conditions to help the user achieve his set goals.

18 Claims, 5 Drawing Sheets

(51) Int. Cl.
  *A61B 5/097*    (2006.01)
  *G01N 33/497*   (2006.01)
  *A61B 5/00*     (2006.01)
  *A61B 5/145*    (2006.01)
  *A61B 5/083*    (2006.01)
  *G01N 33/00*    (2006.01)

(52) U.S. Cl.
  CPC ........ *A61B 5/14546* (2013.01); *A61B 5/4833* (2013.01); *A61B 5/4845* (2013.01); *A61B 5/4866* (2013.01); *A61B 5/7275* (2013.01); *A61B 5/7278* (2013.01); *A61B 5/746* (2013.01); *G01N 33/497* (2013.01); *A61B 5/0022* (2013.01); *A61B 5/083* (2013.01); *A61B 5/097* (2013.01); *A61B 2560/0242* (2013.01); *G01N 33/0075* (2013.01); *G01N 2033/4975* (2013.01)

(56) References Cited

U.S. PATENT DOCUMENTS

| | | | |
|---|---|---|---|
| 2008/0047553 | A1 | 2/2008 | Denyer et al. |
| 2009/0137919 | A1 | 5/2009 | Bar-Lavie et al. |
| 2013/0216989 | A1* | 8/2013 | Cuthbert ............... A61B 5/721 |
| | | | 434/238 |
| 2014/0361900 | A1 | 12/2014 | Nothacker et al. |
| 2014/0378790 | A1* | 12/2014 | Cohen ............... A61B 5/14546 |
| | | | 600/309 |
| 2015/0064672 | A1* | 3/2015 | Bars .................... G01N 33/497 |
| | | | 434/236 |

\* cited by examiner

FIG.4 under 35 U.S.C. § 371 and claims priority from International Application No. PCT/IB16/57537, filed on Dec. 12, 2016, which application claims priority under 35 U.S.C. § 119 from Indian Application No. 4655/MUM/2015, filed on Dec. 10, 2015. The entire contents of the aforementioned application are incorporated herein by reference.

DEVICES AND METHODS FOR NON-INVASIVE MONITORING OF SUBSTANCE IN A BODY

PRIORITY CLAIM

This application is a U.S. National Stage Filing under 35 U.S.C. § 371 and claims priority from International Application No. PCT/IB16/57537, filed on Dec. 12, 2016, which application claims priority under 35 U.S.C. § 119 from Indian Application No. 4655/MUM/2015, filed on Dec. 10, 2015. The entire contents of the aforementioned application are incorporated herein by reference.

TECHNICAL FIELD

The embodiments herein generally relate to monitoring of substance consumption and more particularly to devices and methods that enable goal oriented and personalized monitoring of substance consumption.

BACKGROUND

Substance consumption by a user may be attributed to various reasons such as medical requirement, peer pressure and the like which may easily translate to substance abuse. It is a big challenge to overcome dependence or addiction of substances because it involves more than just good intentions. Abuse of substances must be controlled because of the negative impact it can have on the user. However, it is difficult to monitor consumption patterns and at the same time for the user to remain motivated to continue with a cessation plan. Means such as substance patches, lozenges, gum and sprays are available to help substance users overcome addiction. However, keeping users motivated, side effects of chemicals contained in these means and the fact that there is no monitoring of the substance levels in the body without using invasive techniques continue to pose challenges in cessation plans.

SUMMARY

Embodiments of the present disclosure present technological improvements as solutions to one or more of the above-mentioned technical problems recognized by the inventors in conventional systems.

In an aspect, there is provided a computer implemented method for non-invasive monitoring of substance in a user's body, the method comprising receiving, by an input module, a first data pertaining to substance consumption characteristics based on the substance consumed by the user; identifying, by a dynamic monitoring module, the user's substance consumption profile based on the received first data; and computing, by the dynamic monitoring module, average amount of the substance in the body at a given time ($N_{final}(t)$) based on the received first data.

In an embodiment, the method can further comprise receiving, by the input module, a second data pertaining to the user's profile.

In an embodiment, the step of identifying the user's substance consumption profile comprises receiving a measure of the substance present in the ambience at pre-determined time intervals from the received first data; computing inhale time, hold time and exhale time from the received measure of the substance present in the ambience; computing puff time based on the computed inhale time, hold time and exhale time; and associating the computed puff time with the user's substance consumption profile.

In an embodiment, computing average amount of substance in the body at a given time $N_{final}(t)$ comprises computing substance level in the body after each consumption; and integrating the computed substance level in the body in a day.

In an embodiment, integrating the computed substance level involves use of a unit step function to account for abrupt change in the computed substance levels between consumptions In an embodiment, the method further comprises generating at pre-determined intervals, by a dynamic goal setting module, a summary of consumption of the substance based on the received first data and obtaining goals directed to reduce consumption of the substance by setting desired number of consumptions in a day to be less than the received first data.

In an embodiment, the method further comprises computing, by a dynamic threshold setting module, a threshold N(ICT) corresponding to amount of substance the body can sustain, the threshold N(ICT) being based on the received first data, the received second data and the obtained goals.

In an embodiment, computing the threshold N(ICT) is based on initial quantity of substance in the body ($N_0$), half-life of the substance in the body, residual substance in the body ($N_{res}$) and average time interval between two consecutive consumptions of the substance (ICT).

In an embodiment, the average time interval (ICT) is based on maximum time interval between two consecutive consumptions and number of consumptions of the substance in a day.

In an embodiment, the initial quantity ($N_0$) is computed based on the user's substance consumption profile.

In an embodiment, the half-life of the substance in the body is computed based on the received second data.

In an embodiment, the residual substance in the body ($N_{res}$) is computed based on the computed average amount of substance in the body at a given time ($N_{final}(t)$), the average time interval between two consecutive consumptions of the substance (ICT) and starting time of first consumption of the substance by the user.

In an embodiment, the method further comprises generating and transmitting, by an alerting module, an alert based on a pre-determined condition selected from the group consisting of (i) user consuming the substance before the set threshold N(ICT) is reached by the body, (ii) number of consumptions in a day is more than the desired number of consumptions in the day; and (iii) time interval between two consecutive consumptions of the substance is less than the average time interval between two consecutive consumptions of the substance (ICT).

In another aspect, there is provided a device for non-invasive monitoring amount of substance in a user's body, the device comprising: an input module configured to dynamically receive a first data pertaining to substance consumption characteristics based on the substance consumed by the user; and a dynamic monitoring module configured to identify the user's substance consumption profile and compute average amount of the substance in the body at a given time ($N_{final}(t)$) based on the received first data.

In an embodiment, the input module is further configured to receive a second data pertaining to the user's profile.

In an embodiment, at least some of the first data is received from at least one substance sensor.

In an embodiment, the device further comprises a dynamic goal setting module configured to generate a summary of consumption, at pre-determined intervals, of the substance based on the received first data and obtain goals directed to reduce consumption of the substance by setting desired number of consumptions in a day to be less than the received first data.

In an embodiment, the device further comprises a dynamic threshold setting module configured to compute a threshold N(ICT) corresponding to amount of substance the body can sustain, the threshold N(ICT) being based on the received first data, the received second data and the obtained goals.

In an embodiment, the device further comprises an alerting module configured to generate and transmit an alert based on one or more pre-determined conditions selected from the group consisting of (i) user consuming the substance before the set threshold N(ICT) is reached by the body, (ii) number of consumptions in a day is more than the desired number of consumptions in a day; and (iii) time interval between two consecutive consumptions of the substance is less than the average time interval between two consecutive consumptions of the substance (ICT).

In yet another aspect, there is provided a computer program product for processing data, comprising a non-transitory computer readable medium having program instructions embodied therein for receiving, a first data pertaining to substance consumption characteristics based on the substance consumed by the user; identifying the user's substance consumption profile based on the received first data; and computing average amount of the substance in the body at a given time ($N_{final}(t)$) based on the received first data.

BRIEF DESCRIPTION OF THE DRAWINGS

The embodiments herein will be better understood from the following detailed description with reference to the drawings, in which.

It should be appreciated by those skilled in the art that any block diagram herein represent conceptual views of illustrative devices embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any devices and methods similar or equivalent to those described herein can be used in the practice or testing of embodiments of the present disclosure, the preferred, devices and methods are now described.

Some embodiments of this disclosure, illustrating all its features, will now be discussed in detail. The disclosed embodiments are merely exemplary of the disclosure, which may be embodied in various forms. Before setting forth the detailed explanation, it is noted that all of the discussion below, regardless of the particular implementation being described, is exemplary in nature, rather than limiting.

Referring now to the drawings, and more particularly to FIGS. 1 through 4, where similar reference characters denote corresponding features consistently throughout the figures, there are shown preferred embodiments and these embodiments are described in the context of the following exemplary device and method.

In the context of the present disclosure, the expression "substance" pertains to a chemical substance as known in the art, capable of being consumed by a user and emanating at least a portion of the substance or remnant substance into the ambience of the user, such remnant substance being capable of being sensed and measured by at least one substance sensor. Such substances may be for instance, nicotine that may be consumed in the form of cigarettes, bidis, hookahs, cigars, and the like.

Figure 1:
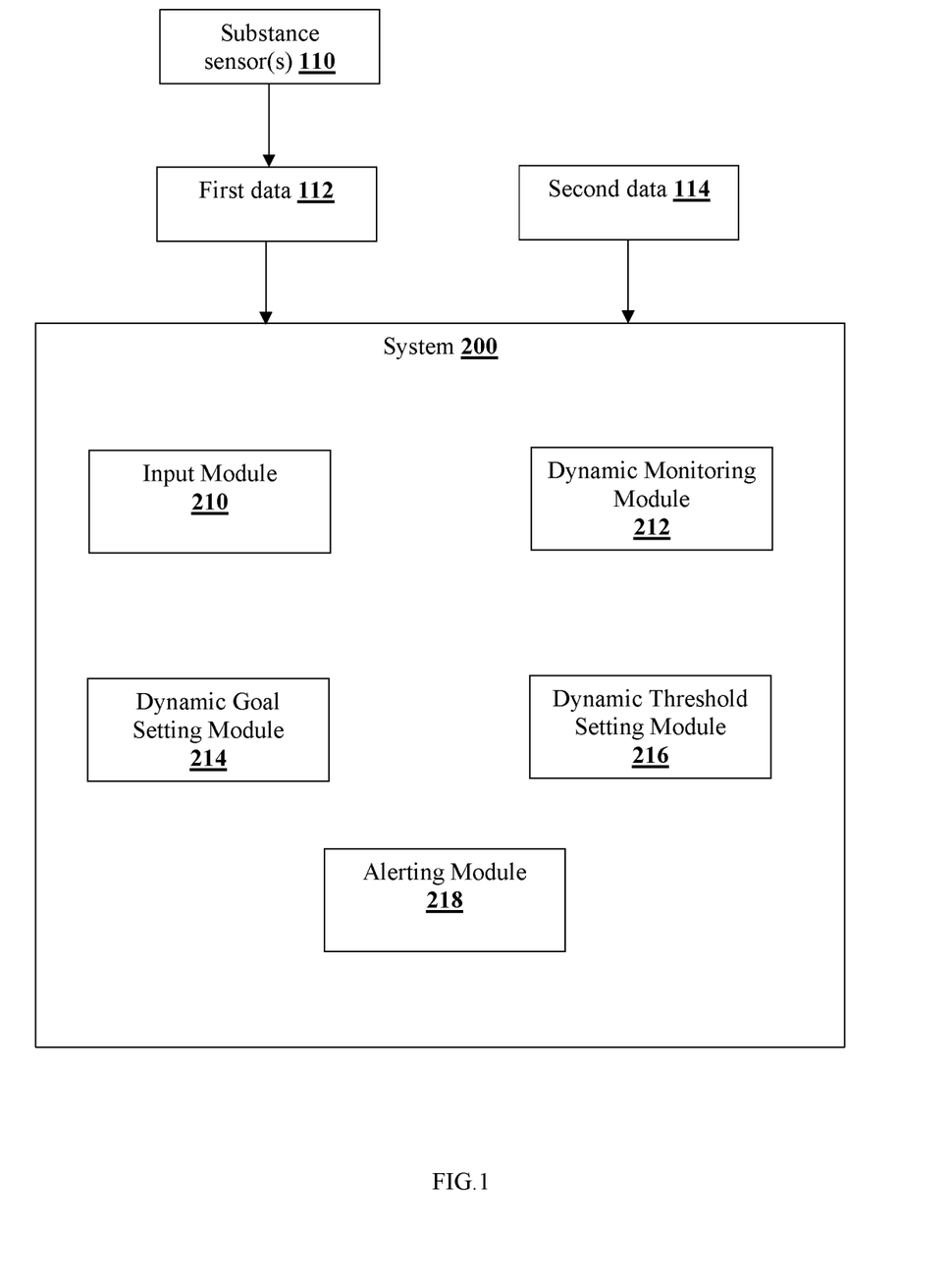
FIG. 1 illustrates an exemplary embodiment of a device for non-invasive monitoring of substance in a user's body in accordance with an embodiment of the present disclosure.
Figure 2:
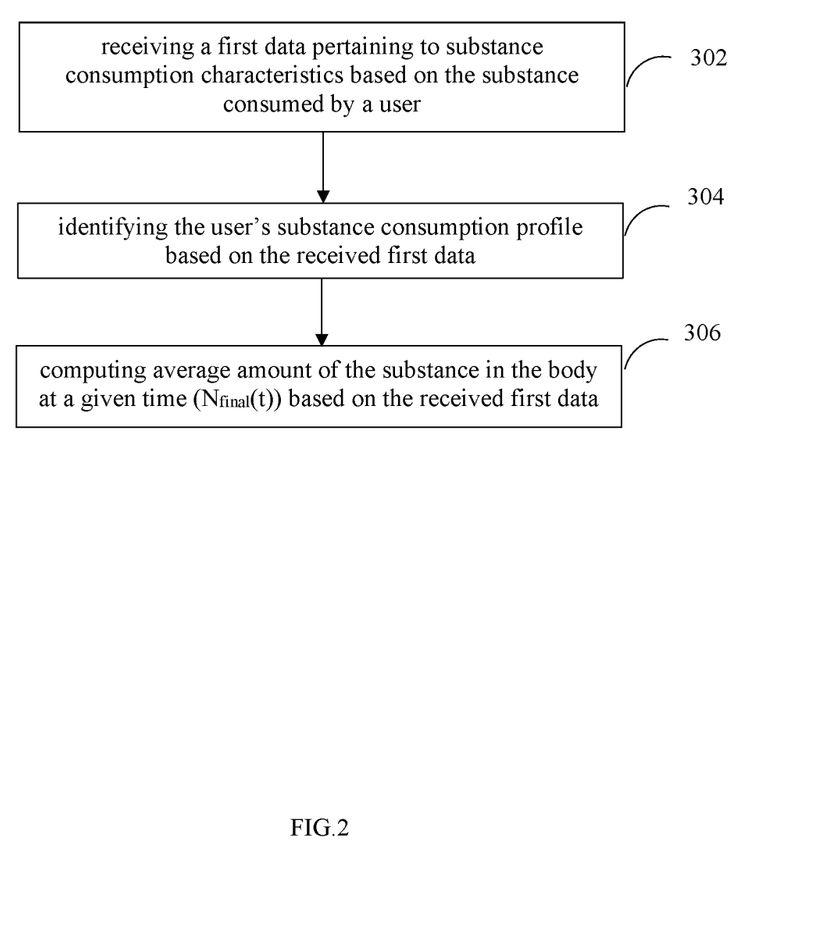
FIG. 2 is an exemplary flow diagram illustrating a computer implemented method for non-invasive monitoring of substance in a user's body in accordance with an embodiment of the present disclosure.

FIG. 1 illustrates an exemplary embodiment of a device 200 for non-invasive monitoring of substance in a user's body and FIG. 2 is an exemplary flow diagram illustrating a computer implemented method for non-invasive monitoring of substance in a user's body using the device 200 in accordance with an embodiment of the present disclosure. In an embodiment, device 100 includes one or more processors (not shown), communication interface or input/output (I/O) interface (not shown), and memory or one or more internal data storage devices (not shown) operatively coupled to the one or more processors. The one or more processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, device 200 can be implemented in a variety of computing systems, such as a laptop computer, a desktop computer, a notebook, a workstation, a mainframe computer, a server, a network server, cloud, hand-held device, wearable device and the like.

The I/O interface can include a variety of software and hardware interfaces, for example, a web interface, a graphical user interface, and the like and can facilitate multiple communications within a wide variety of networks and protocol types, including wired networks, for example, LAN, cable, etc., and wireless networks, such as WLAN, cellular, or satellite. In an embodiment, the I/O interface can include one or more ports for connecting a number of devices to one another or to another server.

The memory may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the various modules of the device 200 can be stored in the memory.

The steps of the computer implemented method of the present disclosure will now be explained with reference to the components of the device 200 as depicted in FIG. 1. At step 302, an input module 210 receives a first data pertaining to substance consumption characteristics based on the substance consumed by the user. The expression "first data" as referred to in the present disclosure refers to one or more of type of substance consumed, number of consumptions per day of the substance, brand name of the consumed substance, time interval between two consecutive consumptions, history of consumption, measure of the substance present in the ambience at pre-determined time intervals, and the like pertaining to the consumption of the substance by the user. In an embodiment, at least some of the first data is received from at least one substance sensor. For instance, in an exemplary embodiment, if the substance is nicotine, the first data can comprise number of cigarettes smoked in a day, brand name of the cigarette consumed, time interval between smoking of two consecutive cigarettes, amount of nicotine in the ambience of the smoker sensed by a nicotine sensor at pre-determined time intervals, and the like. In an embodiment, the nicotine sensor is located in the vicinity of the user.

In an embodiment, the input module 210 is configured to receive a second data pertaining to the user's profile. The expression "second data" as referred to in the present disclosure refers to one or more of age, sex, physical activity levels, health history and the like of the substance user. The second data may be received directly from the user, indirectly through social media, fitness applications or any other source.

At step 304, a dynamic monitoring module 212 identifies the user's substance consumption profile and at step 306, the dynamic monitoring module 212 computes average amount of the substance in the body at a given time, ($N_{final}(t)$) based on the received first data. The step of identifying the user's substance consumption profile comprises receiving a measure of the substance present in the ambience at pre-determined time intervals from the received first data; computing inhale time, hold time and exhale time from the received measure of the substance present in the ambience; computing puff time based on the computed inhale time, hold time and exhale time; and associating the computed puff time with the user's substance consumption profile.

Figure 3A:
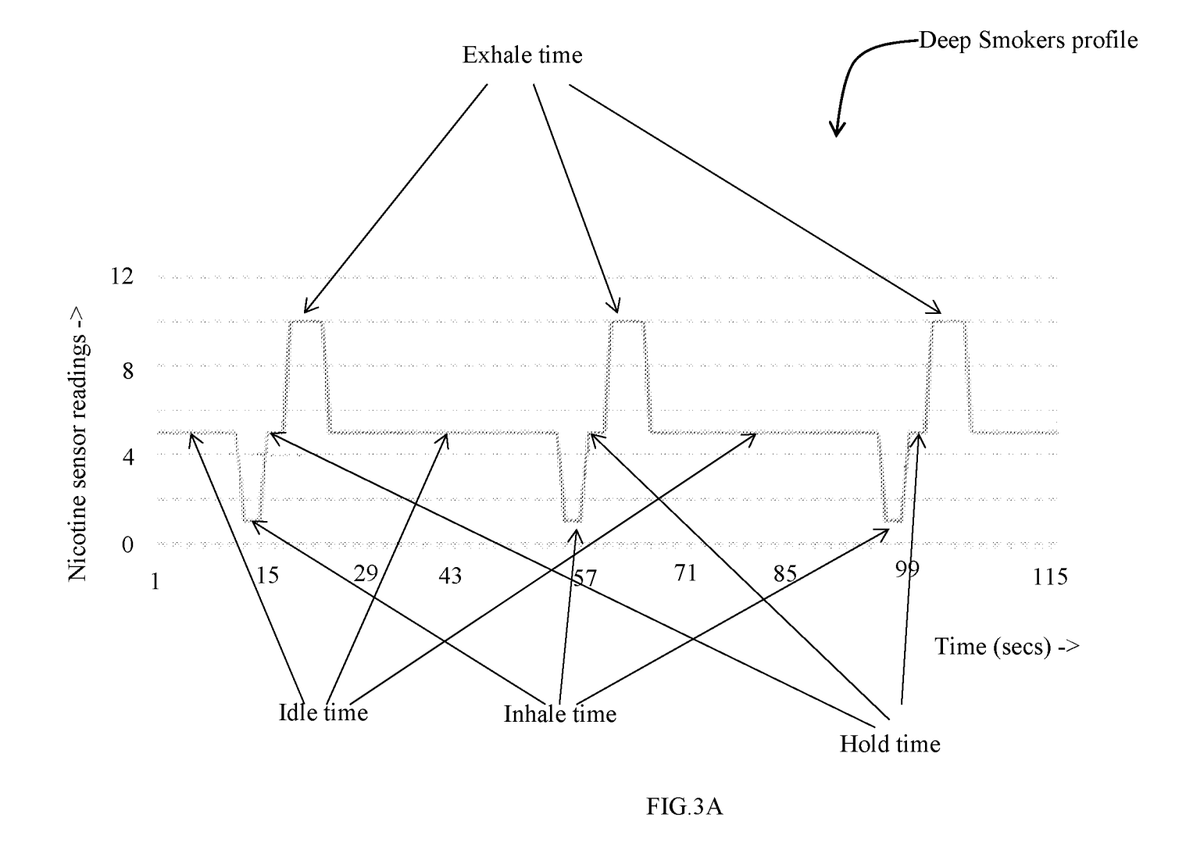
FIGS. 3A and 3B illustrate nicotine sensor readings with respect to time, in an exemplary embodiment of the present disclosure, for a deep smoker and a shallow smoker respectively.
Figure 3B:
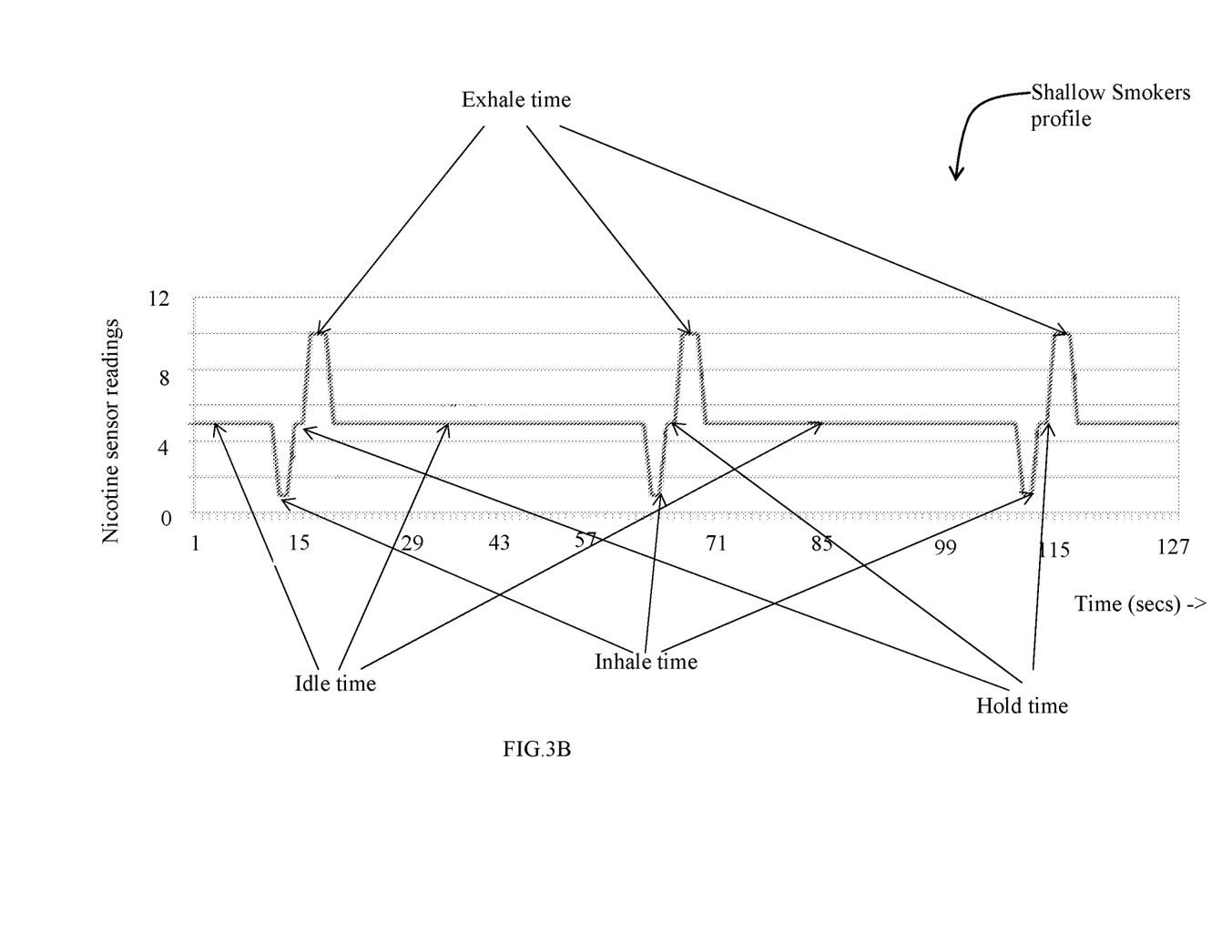

In an exemplary embodiment, wherein the substance is nicotine, identifying the user's nicotine consumption profile can be identified as explained hereinafter. FIGS. 3A and 3B illustrate nicotine sensor readings with respect to time, in an exemplary embodiment of the disclosure for a deep smoker and a shallow smoker respectively. A study conducted on users (smokers) having different nicotine consumption profiles indicates the following with regards to deep and shallow and smokers:

Firstly, the average burning time of a cigarette in smokers hand is:

Cig_burning_time=(360+θ) seconds, wherein −60<θ<+60) depending on the ambient air.

Secondly, smokers follow the following pattern while smoking:
1. Lit—time when the cigarette is lit
2. Inhale—time when smoker inhales smoke
3. Hold—time when smokers holds smoke inside his body
4. Exhale—time when smokers exhale smoke
5. Idle—waiting time for next puff
6. Repeat from step 2 to step 5 until the cigarette completely burns out The following table shows approximate time lines for a shallow and deep smoker:

| Time in sec ⟹ | | | | | |
|---|---|---|---|---|---|
| Smoking profile ⬇ | Inhale | Hold | Exhale | Idle | Number of puffs (approx.) |
| Shallow | 2 | 1-2 | 3 | 40 | 7 |
| Deep | 3 | 3 | 5 | 30 | 9 |

FIGS. 3A and 3B and the above table indicate that the inhale time/hold time/exhale time constitute important measures to distinguish different smoking profiles. Based on the received measure of nicotine present in the ambience, as sensed by a nicotine sensor, at pre-determined time intervals, the inhale time, hold time and exhale time are computed.

$$\text{Puff time}[i]=\text{inhale time}[i]+\text{hold time}[i]+\text{exhale time}[i]$$

where,
i=puff number (for instance first puff, second puff, and the like)
Puff time [i]=puff time for $i^{th}$ puff.
Inhale time [i]=inhale time of $i^{th}$ puff
Hold time [i]=hold time of $i^{th}$ puff
Exhale time [i]=exhale time of $i^{th}$ puff Based on the computed puff time the smoker's nicotine consumption profile can be identified. For instance,
1. If the puff time of smoker<=puff time of shallow smoker (from table 3.1) ➔ smoker is identified as a shallow smoker
2. If the puff time of smoker>=puff time of deep smoker (from table 3.1) ➔ smoker is identified as a deep smoker
3. If the puff time of smoker is in between puff time of deep and shallow smoker (from table 3.1) ➔ smoker is identified as a medium smoker.

Thus the computed puff time can be associated with the user's substance consumption profile It is assumed that output of the nicotine sensor is proportional to the volume of smoke generated when the user smokes. If $N_0$ or the "initial quantity" refers to the average amount of intake of the substance that is nicotine in this exemplary instance, each time the user smokes, and if tobacco weight in a cigarette/bidi is represented as $T_{wt}$, average nicotine content $N_0$ is represented as given below.

| Type | Avg. nicotine content |
| --- | --- |
| Cigarette | 1.5% $T_{wt}$ |
| Bidi | 2% $T_{wt}$ |

Average nicotine intake range varies from 5% to 30% of average nicotine content. Based on empirical study, the average intake varies with smoking style as represented below.

| Smoking profile | % of Avg. nicotine intake ($N_0$) |
| --- | --- |
| Deep inhaler | 20 |
| Medium inhaler | 15 |
| Shallow inhaler | 10 |

For example,
Let tobacco weight of cigarette is, $T_{wt}$=700 mg

Average nicotine content = 1.5% of $T_{wt}$ = 0.015 * 700 mg = 10.5 mg

= 10 mg (for simplicity)

Avg. nicotine intake varies from 5%-30% of avg nicotine content i.e. 0.5 mg-3 mg. Therefore the average intake based on smoking profile varies as represented below.

| Smoking profile | Avg. nicotine intake ($N_0$ in mg) |
| --- | --- |
| Deep inhaler | 2 |
| Medium inhaler | 1.5 |
| Shallow inhaler | 1 |

The step of computing average amount of substance in the user's body at a given time $N_{final}(t)$ comprises computing substance level in the body after each consumption; and integrating the computed substance level in the body in a day. In an exemplary embodiment, wherein the substance is nicotine, ($N_{final}(t)$) can be computed as explained hereinafter. Nicotine level in the body decays exponentially and its half-life varies between 1-2 hours as known in the art. Therefore, nicotine level N(t) in the body at a given time t can be calculated as known in the art as:

$$N(t) = N_0 * \left(\frac{1}{2}\right)^{\frac{t}{t_{\frac{1}{2}}}} = N_0 * e^{-\frac{t}{\tau}} = N_0 * e^{-\lambda t}$$

wherein $N_0$ or the "initial quantity" refers to the average amount of intake of the substance that is nicotine in this exemplary instance, each time the user smokes, $t_{1/2}$ refers to half-life of nicotine, $\lambda$ refers to decay constant of nicotine and $\tau$ refers to mean lifetime of nicotine in this exemplary instance.

The relationship between $t_{1/2}$, $\lambda$, and $\tau$ as known in the art is expressed as:

$$t_{1/2} = \frac{\ln(2)}{\lambda} = \tau \ln(2)$$

Figure 4:
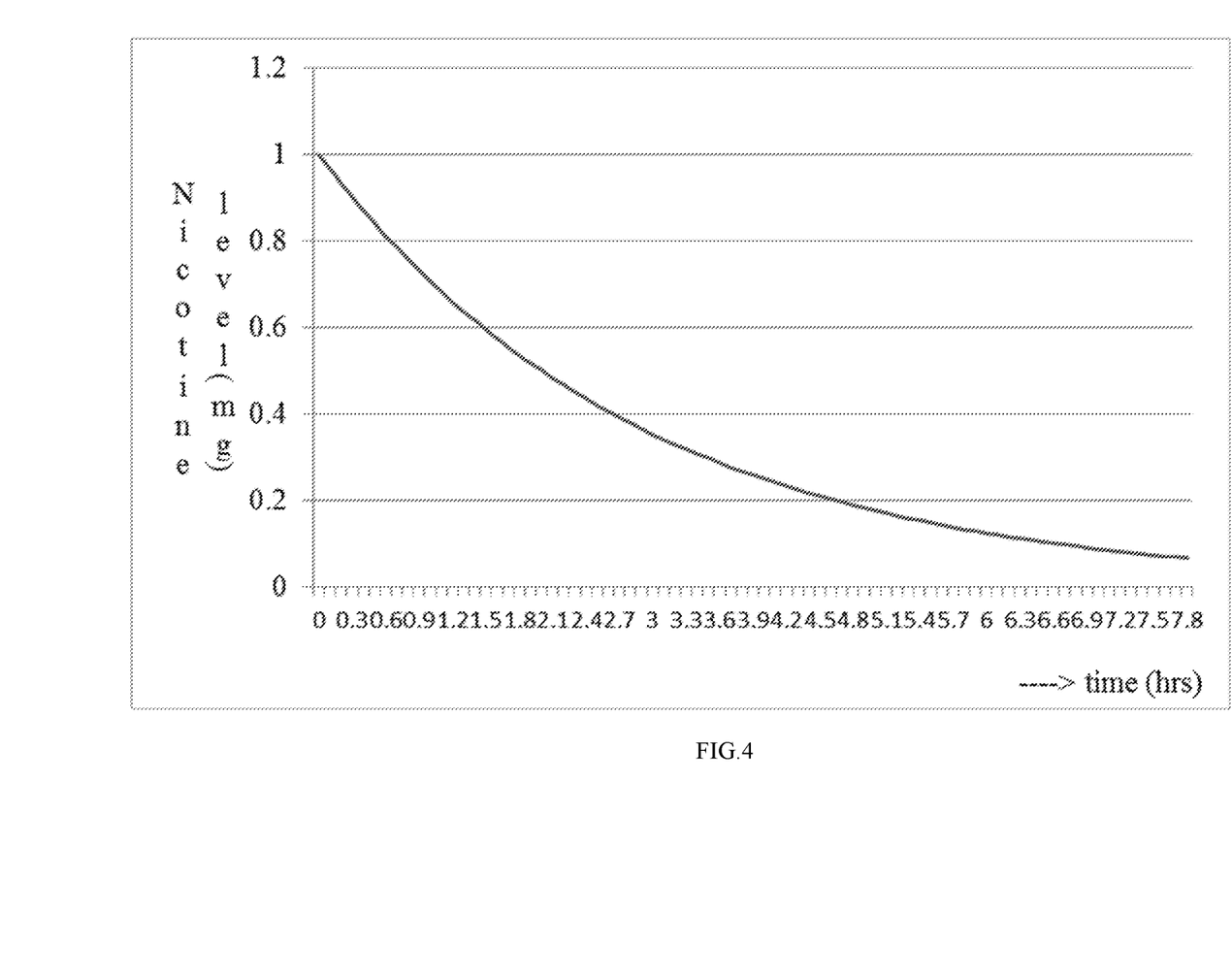
FIG. 4 illustrates nicotine sensor readings with respect to time, in an exemplary embodiment of the disclosure.

FIG. 4 illustrates nicotine level variations with respect to time, as known in the art, for an exemplary half-life of 2 hours and initial quantity $N_0$ is 1 mg, wherein nicotine level N(t) in the body at a given time t can be expressed as:

$$N(t) = N_0 * \left(\frac{1}{2}\right)^{\frac{t}{t_{\frac{1}{2}}}} \text{ or } N(t) = 1 * \left(\frac{1}{2}\right)^{\frac{t}{2}}$$

In an embodiment, integrating the substance level in the body in a day involves use of a unit step function u(t) to account for abrupt change in the computed substance levels between consumptions. In an exemplary embodiment, this can be expressed as:

$$N(t) = u(t) * N_0 * \left(\frac{1}{2}\right)^{\frac{t}{t_{\frac{1}{2}}}}$$

wherein, $$u(t) = \begin{cases} 1, \text{ for } t \geq 0 \\ 0, \text{ for } t < 0 \end{cases}$$

If the user smokes at a time $t_1$, then the nicotine level starts decaying exponentially from the initial quantity $N_0$ obtained after a smoke. Hence nicotine level $N_1(t)$ in the body after the first smoke can be expressed as:

$$N_1(t) = N(t - t_1) = u(t - t_1) * N_0 * \left(\frac{1}{2}\right)^{\frac{t-t_1}{t_{\frac{1}{2}}}}$$

If the user smokes at time $t_2$ again, then the nicotine level starts decaying exponentially again from the initial quantity $N_0$ obtained after the second smoke. Hence nicotine level $N_2(t)$ in the body after the second smoke can be expressed as:

$$N_2(t) = N(t - t_2) = u(t - t_2) * N_0 * \left(\frac{1}{2}\right)^{\frac{t-t_2}{t_{\frac{1}{2}}}}$$

The above expressions can be obtained for nicotine levels after every smoke by the user.

Therefore, the average amount of the substance in the body at a given time, $N_{final}(t)$ can be expressed as:

$$N_{final}(t) = N_1(t) + N_2(t) + N_3(t) + \cdots + N_k(t)$$

$$\Longrightarrow N_{final}(t) = N(t - t_1) + N(t - t_2) + \cdots + N(t - t_k)$$

$$\Longrightarrow N_{final}(t) = u(t - t_1) * N_0 * \left(\frac{1}{2}\right)^{\frac{t-t_1}{t_{\frac{1}{2}}}} +$$

$$u(t - t_2) * N_0 * \left(\frac{1}{2}\right)^{\frac{t-t_2}{t_{\frac{1}{2}}}} + \cdots + i(t - t_k) * N_0 * \left(\frac{1}{2}\right)^{\frac{t-t_k}{t_{\frac{1}{2}}}}$$

$$\Longrightarrow N_{final}(t) = \Sigma_{i=1}^{k} u(t - t_i) * N_0 * \left(\frac{1}{2}\right)^{\frac{t-t_i}{t_{\frac{1}{2}}}}$$

$$\Longrightarrow N_{final}(t) = \Sigma_{i=1}^{k} N(t - t_i)$$

Thus the average amount of the substance in the body at a given time, $N_{final}(t)$ can be computed at any given time t for k number of consumptions.

In an embodiment, the device 200 further comprises a dynamic goal setting module 214 configured to generate a summary of consumption, at pre-determined intervals, of the substance based on the received first data and obtain goals directed to reduce consumption of the substance by setting desired number of consumptions in a day to be less than the received first data. In an exemplary embodiment wherein the substance is nicotine, the user can receive a summary of his smoking history using which the user can set goals for a fixed duration such as maximum number of cigarettes to be smoked per day with the intent of reducing the intake from his current intake.

In an embodiment, the device 200 further comprises a dynamic threshold setting module 216 configured to compute a threshold N(ICT) corresponding to amount of substance the body can sustain, the threshold N(ICT) being based on the received first data, the received second data and the obtained goals. In an embodiment, the threshold N(ICT) is based on the initial quantity of substance in the body ($N_0$), half-life of the substance in the body ($t_{1/2}$), residual substance in the body ($N_{res}$) and average time interval between two consecutive consumptions of the substance (ICT).

In an exemplary embodiment wherein the substance is nicotine, half-life of the nicotine in the body $t_{1/2}$ ranges from 1 to 2 hours or $t_{1/2} \rightarrow [1,2]$.

Let $t_{1/2} = 1, t_{1/2max} = 2$ and $t_{1/2avg} = (t_{1/2min} + t_{1/2max})/2$ Based on empirical study, the following table describes $t_{1/2}$ based on the second data such as physical activity of the user.

| Physical activity | $t_{1/2}$ |
|---|---|
| Athlete | $t_{1/2min}$ |
| Normal work-out | $t_{1/2avg}$ |
| No workout | $t_{1/2max}$ |

In the exemplary embodiment wherein the substance is nicotine, from the received first data, number of cigarettes smoked per day ($N_{cd}$) and maximum time interval between two consecutive cigarette smoking ($t_m$) are determined. The average time interval between two consecutive consumptions of the substance, nicotine in this case is represented by ICT or Inter Cigarette Time is based on the maximum time interval between two consecutive consumptions and the number of consumptions of the substance in a day and can be represented as:

$$ICT = \frac{60 * (24 - t_m)}{(N_{cd} - 1)}$$

In accordance with the present disclosure, the threshold N(ICT) corresponding to amount of substance the body can sustain can be computed as N(T) at t=ICT.

$$N(ICT) = (N_{res} + N_0) * \left(\frac{1}{2}\right)^{\frac{ICT}{t_1}}$$

wherein $N_{res}$ refers to the residual substance in the body or the accumulated amount of the substance or nicotine in the body based on the received first data.

In an embodiment, $N_{res}$ is computed using the average amount of nicotine in the body in a day, $N_{final}(t)$ If $t_i$ represents start time of $i^{th}$ cigarette and ST represents starting time for the first cigarette in a day, then $$t_i = ST + i * ICT$$

wherein i represents cigarette number consumed by the user, for instance, 1, 2, 3, ... k (k=$N_{od}$)
Thus, $N_{res}$ computed based on the smoking history of the user can be computed as:

$$N_{res} = \sum_{\substack{all\ days\ of \\ smoking\ history}} N_{final}(t)$$

In an embodiment, the device 200 further comprises an alerting module 218 configured to generate and transmit an alert based on one or more pre-determined conditions selected from the group consisting of (i) user consuming the substance before the set threshold N(ICT) is reached by the body, (ii) number of consumptions in a day is more than the desired number of consumptions in a day; and (iii) time interval between two consecutive consumptions of the substance is less than the average time interval between two consecutive consumptions of the substance (ICT).

Thus, devices and methods in accordance with various embodiments of the present disclosure provide a goal oriented personalized monitoring of substance consumed by a user in a non-invasive manner. Initially user can set his goals based on his substance consumption history which will be targeted to reduce the number of intake. As the user reaches his goal successfully, he will be motivated through personalized alerts to modify the goals to further reduce the substance intake. This eventually helps the user to overcome addiction to substances that are prone to have harmful effects on the body and mind. Devices and methods of the present disclosure enable identifying the user's consumption profile effectively and also facilitates computation of the Inter Cigarette Time (ICT) and the threshold corresponding to the amount of substance the user's body can sustain to provide personalized monitoring of the substance consumed by the user.

The written description describes the subject matter herein to enable any person skilled in the art to make and use the embodiments of the invention. The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the invention may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules comprising the device of the present disclosure and described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The various modules described herein may be implemented as software and/or hardware modules and may be stored in any type of non-transitory computer readable medium or other storage device. Some non-limiting examples of non-transitory computer-readable media include CDs, DVDs, BLU-RAY, flash memory, and hard disk drives.

Further, although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A device for non-invasive monitoring amount of substance in a user's body, the device comprising:
    an input module configured to dynamically receive a first data pertaining to substance consumption characteristics based on the substance consumed by the user, wherein at least some of the first data is received from at least one substance sensor, and the first data comprises a measure of the substance present in an ambiance of the user at predetermined time intervals, wherein the substance is a chemical substance capable of being consumed by the user and emanating at least a portion of the substance or remnant substance into the ambience of the user, and wherein the remnant substance being capable of sensed and measured by the substance sensor; and
    a dynamic monitoring module configured to identify the user's substance consumption profile and compute average amount of the substance in the body at a given time ($N_{final}(t)$) based on the received first data, wherein the user's substance consumption profile is identified by:
        computing inhale time, hold time and exhale time from the received measure of the substance present in the ambience;
        computing puff time based on the computed inhale time, hold time and exhale time; and
        associating the computed puff time with the user's substance consumption profile; and
    wherein the average amount of substance in the body at the given time $N_{final}(t)$ is computed by:
        computing substance level in the body after each consumption; and
        integrating the computed substance level in the body in a day.

2. The device of claim 1, wherein the input module is further configured to receive a second data pertaining to the user's profile.

3. The device of claim 2 further comprising a dynamic goal setting module configured to generate a summary of consumption, at pre-determined intervals, of the substance based on the received first data and obtain goals directed to reduce consumption of the substance by setting desired number of consumptions in a day to be less than the received first data.

4. The device of claim 3 further comprising a dynamic threshold setting module configured to compute a threshold N(ICT) corresponding to amount of substance the body can sustain, the threshold N(ICT) being based on the received first data, the received second data and the obtained goals.

5. The device of claim 4, wherein the dynamic threshold setting module is further configured to compute the threshold N(ICT) based on initial quantity of substance in the body ($N_0$), half-life of the substance in the body, residual substance in the body ($N_{res}$) and average time interval between two consecutive consumptions of the substance (ICT).

6. The device of claim 5 further comprising an alerting module configured to generate and transmit an alert based on one or more pre-determined conditions selected from the group consisting of (i) user consuming the substance before the set threshold N(ICT) is reached by the body, (ii) number of consumptions in a day is more than the desired number of consumptions in a day; and (iii) time interval between two consecutive consumptions of the substance is less than the average time interval between two consecutive consumptions of the substance (ICT).

7. A computer implemented method for non-invasive monitoring of substance in a user's body, the method comprising:
    receiving, by an input module, a first data pertaining to substance consumption characteristics based on the substance consumed by the user, wherein at least some of the first data is received from at least one substance sensor, and the first data comprises a measure of the substance present in an ambiance of the user at predetermined time intervals, wherein the substance is a chemical substance capable of being consumed by the user and emanating at least a portion of the substance or remnant substance into the ambience of the user, and wherein the remnant substance being capable of sensed and measured by the substance sensor;
    identifying, by a dynamic monitoring module, the user's substance consumption profile based on the received first data, wherein the user's substance consumption profile is identified by:
        computing inhale time, hold time and exhale time from the received measure of the substance present in the ambience;
        computing puff time based on the computed inhale time, hold time and exhale time; and
        associating the computed puff time with the user's substance consumption profile; and
    computing, by the dynamic monitoring module, average amount of the substance in the body at a given time ($N_{final}(t)$) based on the received first data, wherein the average amount of substance in the body at the given time $N_{final}(t)$ is computed by:
  computing substance level in the body after each consumption; and
  integrating the computed substance level in the body in a day.

8. The computer implemented method of claim 7 further comprising receiving, by the input module, a second data pertaining to the user's profile.

9. The computer implemented method of claim 8 further comprising performing at least one of:
  generating at pre-determined intervals, by a dynamic goal setting module, a summary of consumption of the substance based on the received first data and obtaining goals directed to reduce consumption of the substance by setting desired number of consumptions in a day to be less than the received first data; and
  computing, by a dynamic threshold setting module, a threshold N(ICT) corresponding to amount of substance the body can sustain, the threshold N(ICT) being based on the received first data, the received second data and the obtained goals.

10. The computer implemented method of claim 9, wherein computing the threshold N(ICT) is based on initial quantity of substance in the body ($N_0$), half-life of the substance in the body, residual substance in the body ($N_{res}$) and average time interval between two consecutive consumptions of the substance (ICT).

11. The computer implemented method of claim 10, wherein the average time interval (ICT) is based on maximum time interval between two consecutive consumptions and number of consumptions of the substance in a day.

12. The computer implemented method of claim 10 wherein the initial quantity ($N_0$) is computed based on the user's substance consumption profile.

13. The computer implemented method of claim 10, wherein the half-life of the substance in the body is computed based on the received second data.

14. The computer implemented method of claim 10, wherein the residual substance in the body ($N_{res}$) is computed based on the computed average amount of substance in the body at a given time ($N_{final}(t)$), the average time interval between two consecutive consumptions of the substance (ICT) and starting time of first consumption of the substance by the user.

15. The computer implemented method of claim 10 further comprising generating and transmitting, by an alerting module, an alert based on a pre-determined condition selected from the group consisting of (i) user consuming the substance before the set threshold N(ICT) is reached by the body, (ii) number of consumptions in a day is more than the desired number of consumptions in the day; and (iii) time interval between two consecutive consumptions of the substance is less than the average time interval between two consecutive consumptions of the substance (ICT).

16. The computer implemented method of claim 7, wherein identifying the user's substance consumption profile comprises:
  receiving a measure of the substance present in the ambience at pre-determined time intervals from the received first data.

17. The computer implemented method of claim 7, wherein integrating the computed substance level involves use of a unit step function to account for abrupt change in the computed substance levels between consumptions.

18. A computer program product comprising a non-transitory computer readable medium having a computer readable program embodied therein, wherein the computer readable program, when executed on a computing device, causes the computing device to:
  receive a first data pertaining to substance consumption characteristics based on the substance consumed by the user, wherein at least some of the first data is received from at least one substance sensor, and the first data comprises a measure of the substance present in an ambiance of the user at predetermined time intervals, wherein the substance is a chemical substance capable of being consumed by the user and emanating at least a portion of the substance or remnant substance into the ambience of the user, and wherein the remnant substance being capable of sensed and measured by the substance sensor;
  identify, the user's substance consumption profile based on the received first data, wherein the user's substance consumption profile is identified by:
    computing inhale time, hold time and exhale time from the received measure of the substance present in the ambience;
    computing puff time based on the computed inhale time, hold time and exhale time; and
    associating the computed puff time with the user's substance consumption profile;
  compute, an average amount of the substance in the body at a given time ($N_{final}(t)$) based on the received first data, wherein the average amount of substance in the body at the given time $N_{final}(t)$ is computed by:
    computing substance level in the body after each consumption; and
    integrating the computed substance level in the body in a day;
  receive a second data pertaining to the user's profile;
  generate at pre-determined intervals, a summary of consumption of the substance based on the received first data and obtain goals directed to reduce consumption of the substance by setting desired number of consumptions in a day to be less than the received first data;
  compute, a threshold N(ICT) corresponding to amount of substance the body can sustain, the threshold N(ICT) being based on the received first data, the received second data and the obtained goals; and
  generate and transmit, an alert based on a pre-determined condition selected from the group consisting of (i) user consuming the substance before the set threshold N(ICT) is reached by the body, (ii) number of consumptions in a day is more than the desired number of consumptions in the day; and (iii) time interval between two consecutive consumptions of the substance is less than the average time interval between two consecutive consumptions of the substance (ICT).

* * * * *